United States Patent
Bohl et al.

(10) Patent No.: US 11,096,698 B2
(45) Date of Patent: Aug. 24, 2021

(54) APPARATUS AND BONE CUTTING DEVICE FOR REMOVAL OF BONE TISSUE

(71) Applicant: DIGNITY HEALTH, San Francisco, CA (US)

(72) Inventors: Michael Bohl, San Francisco, CA (US); Iridian Vaca, San, CA (US); Ryan Samuel Schulte, San Francisco, CA (US); Andrew Robert Bruce, San Francisco, CA (US); Leah Elizabeth Fletcher, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 17/040,337

(22) PCT Filed: Mar. 22, 2019

(86) PCT No.: PCT/US2019/023614
§ 371 (c)(1),
(2) Date: Sep. 22, 2020

(87) PCT Pub. No.: WO2019/183491
PCT Pub. Date: Sep. 26, 2019

(65) Prior Publication Data
US 2021/0015499 A1 Jan. 21, 2021

Related U.S. Application Data

(60) Provisional application No. 62/646,766, filed on Mar. 22, 2018.

(51) Int. Cl.
*A61B 17/00* (2006.01)
*A61B 17/17* (2006.01)
(Continued)

(52) U.S. Cl.
CPC .............. *A61B 17/17* (2013.01); *A61B 17/15* (2013.01); *A61B 17/1604* (2013.01);
(Continued)

(58) Field of Classification Search
None
See application file for complete search history.

(56) References Cited

U.S. PATENT DOCUMENTS

| 4,586,496 A | 5/1986 | Keller |
| 5,171,245 A | 12/1992 | Cezana |

(Continued)

FOREIGN PATENT DOCUMENTS

| CN | 201312823 Y | 9/2009 |
| WO | 2018144611 A1 | 8/2018 |

OTHER PUBLICATIONS

International Search Report and Written Opinion issued in Application No. PCT/US2019/023614, dated Jul. 29, 2019, 12 pages.

*Primary Examiner* — Sameh R Boles
(74) *Attorney, Agent, or Firm* — Polsinelli PC

(57) ABSTRACT

Embodiments of a device for forming incisions and extracting osseous tissue are disclosed. The device includes a body defining a channel. A blade is oriented in linear sliding engagement within the channel of the body. The device includes a stopping mechanism for restricting movement of the blade relative to the body. The device is engageable to an apparatus. The apparatus includes a fixed portion that defines a first end and a second end. A clamp is oriented along the fixed portion of the apparatus adjacent the device. The clamp and the device are collectively configured to remove bone tissue from a patient.

13 Claims, 15 Drawing Sheets

(51) Int. Cl.
    *A61B 17/15*     (2006.01)
    *A61B 17/16*     (2006.01)
    *A61B 17/32*     (2006.01)
    *A61B 17/3211*   (2006.01)
    *A61B 18/20*     (2006.01)

(52) U.S. Cl.
    CPC ....... *A61B 17/1671* (2013.01); *A61B 17/1757* (2013.01); *A61B 17/3211* (2013.01); *A61B 17/320068* (2013.01); *A61B 18/20* (2013.01)

(56) References Cited

U.S. PATENT DOCUMENTS

2005/0273167 A1    12/2005    Triplett et al.
2017/0042566 A1*    2/2017    Mirza .............. A61B 17/32002

* cited by examiner

US 11,096,698 B2

APPARATUS AND BONE CUTTING DEVICE FOR REMOVAL OF BONE TISSUE

CROSS REFERENCE TO RELATED APPLICATIONS

This is a non-provisional application that claims benefit to U.S. provisional application Ser. No. 62/646,766, filed on Mar. 22, 2018, which is herein incorporated by reference in its entirety.

FIELD

The present disclosure generally relates to medical apparatuses and devices, and in particular to surgical apparatuses configured for incision and extraction of osseous tissue that includes a clamp and bone cutting devices arranged along a fixed portion of the apparatus.

BACKGROUND

Various surgical procedures may involve the removal of osseous tissue, or bone. Such procedures may include, e.g., incisions along portions of the rib cage to gain access to the thoracic cavity, removal of bone tissue during knee surgery, or removal of portions of the skull or cutting of the skull during brain surgery. In most cases, precise and measureable cuts are required for each procedure. However, conventional devices typically employed for these procedures may lack precision and sufficient stabilization features, or have other drawbacks which may increase the likelihood of complications or concerns during surgery.

As one specific example, a laminectomy is a surgical procedure for removal of the vertebral arch, located in the cervical, thoracic, lumbar, and sacral regions of the spine. This procedure may be performed on patients with back pain due to compression along the spinal cord or nerves, which may be caused from various spine diseases, including (but not limited to) degenerative, infectious, neoplastic, traumatic, and congenital pathologies. Removal of the vertebral arch allows for decompression of the spinal canal, and gives the surgeon access to the contents of the spinal canal as needed. It is important when performing a laminectomy not to harm or tear the dura mater, which is a layer of tissue that surrounds and protects the spinal cord and nerve roots. A tear of the dura mater (fibrous sac containing the spinal cord, nerve roots, and spinal fluid) can result in cerebrospinal fluid leakage, which can potentially inhibit the body's healing process while also increasing the probability of an infection. With conventional surgical instruments used in this space, removal of the vertebral arch without causing a dural tear remains difficult. Further, such conventional instruments require an applied force to break through the vertebrae. This force is also generally unrestricted, thereby forfeiting the ability to control precision.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
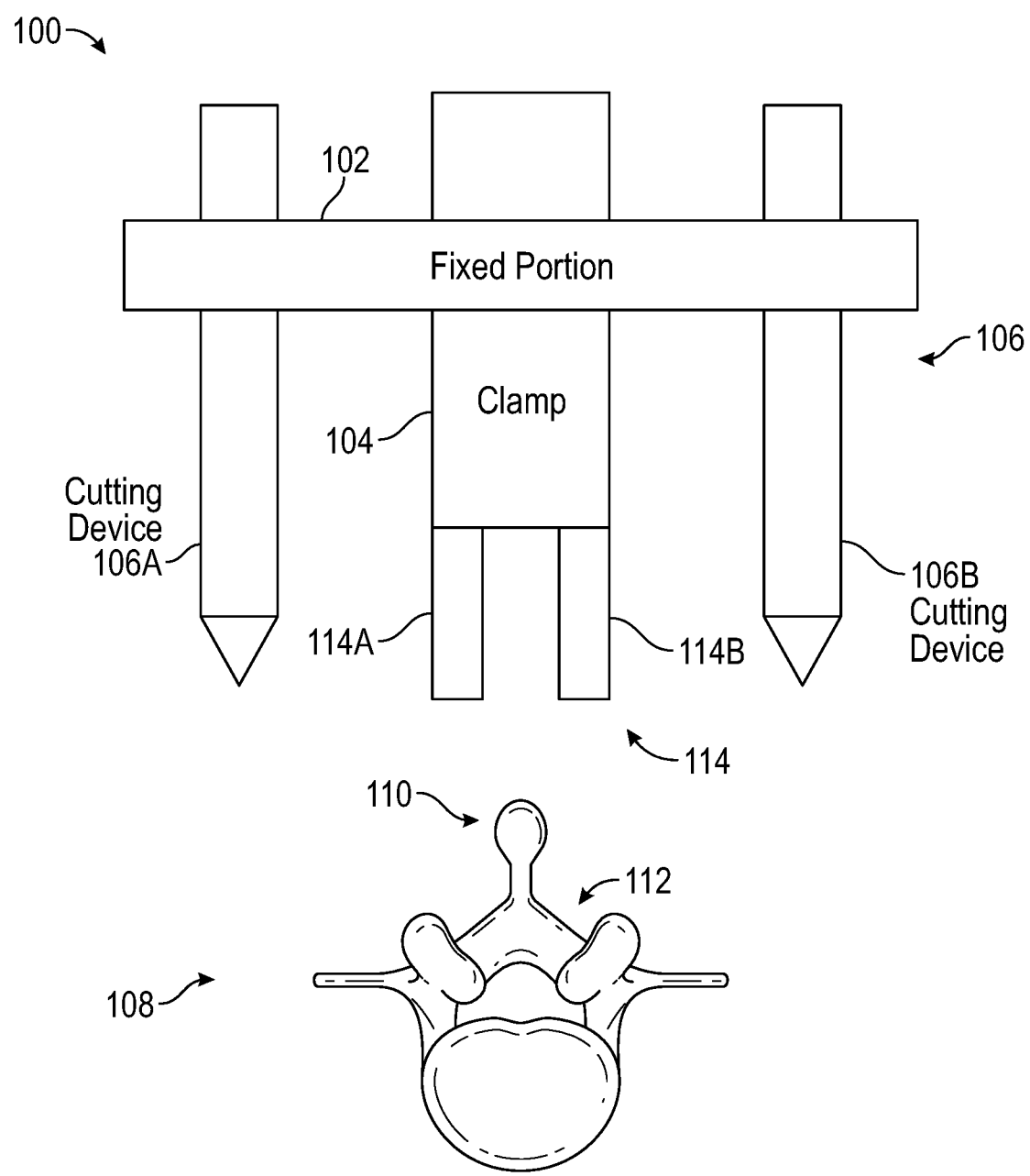
FIG. 1 is a simplified block diagram of an apparatus for incision and extraction of osseous tissue, according to aspects of the present disclosure.

The present disclosure relates to an apparatus and associated devices for incision and extraction of osseous tissue, which may also be referred to interchangeably herein as bone tissue. More specifically, an apparatus as described herein may include a fixed portion, a clamp mechanically coupled to the fixed portion for gripping bone tissue during a surgical procedure, and one or more (e.g., a plurality of) bone cutting devices arranged around the clamp along the fixed portion for cutting osseous tissue. In some embodiments, the bone cutting devices may include spring-loaded blades, and in other embodiments, the bone cutting devices may include blades coupled to rods and linear ball bearings; the blades configured for controlled reciprocating motion along a body.

In addition, in some embodiments, the clamp, and the plurality of bone cutting devices may be engaged to the fixed portion using linear and spherical joints so that the clamp and bone cutting devices may be oriented along different horizontal and vertical axes relative to the fixed portion. Referring to the drawings, embodiments of an apparatus for incision and extraction of osseous tissue are illustrated and generally indicated as 100, 200, and 300 in FIGS. 1-15.

Referring to FIG. 1, a first embodiment of an apparatus, designated 100, includes a fixed portion 102, a clamp 104 coupled to the fixed portion 102, and a plurality of bone cutting devices 106, illustrated as cutting device 106A and cutting device 106B, that are coupled to the fixed portion 102 and oriented around the clamp 104, such that the clamp 104 is positioned between the cutting device 106A and the cutting device 106B. It should be understood that a pair of bone cutting devices 106 is shown solely for demonstration purposes, and some embodiments may include one bone cutting device or more than two bone cutting devices as needed for specific applications.

In some embodiments, the fixed portion 102 may comprise an elongated member, a rod, a linear guide rail, or a frame. The fixed portion 102 may be generally oriented to extend horizontally over a bone such as a vertebra 108 of a patient, including a spinous process 110 and lamina 112, as shown. During use, the fixed portion 102 generally rests in a fixed, stationary position relative to the other components of the apparatus 100 and the target bone, as described herein.

As shown, the clamp 104 may be coupled in a generally central position along the fixed portion 102. The clamp 104 may include any form of clamping device or vise-like apparatus capable of engaging and gripping a target area of bone tissue, such as the spinous process 110. In some embodiments, the clamp 104 may be coupled to the fixed portion 102 using a spherical joint or hinge joint (not shown) so that clamp 104 may be oriented along different horizontal and vertical axes relative to the fixed portion 102 or be configured with multiple degrees of freedom. In some embodiments, the clamp 104 may also be in linear sliding engagement along the fixed portion 102 (not shown). In other embodiments, the clamp 104 may be coupled to the fixed portion 102 using a vertically aligned support member (not shown). Yet in other embodiments, the clamp 104 may be fixed in a stationary position relative to the fixed portion 102.

In some embodiments, the clamp 104 includes at least a pair of clamp legs 114 illustrated as a first claim leg 114A and a second clamp leg 114B. The first clamp leg 114A and the second clamp leg 114B may be driven or moved together to bind or grip the spinous process 110 or other bone matter. Movement of the clamp legs 114 may be achieved by tightening a screw (not shown) in mechanical engagement with the clamp legs 114, or the clamp legs 114 may be spring loaded such that the clamp legs 114 are biased to a closed configuration, and may be driven to an open configuration by releasing the spring (not shown). Other suitable methods of moving the clamp legs 114 are contemplated and described herein. In other embodiments, a C-clamp may be implemented which is devoid of multiple legs and generally involves drawing a movable closing member against a stationary member to hold an object in place. Other such clamps are contemplated by the present inventive disclosure.

The bone cutting devices 106 are configured and operable to cut bone tissue and may include at least one of a drill, an osteotome, a rongeur, a scalpel, a laser, an ultrasonic device, a chisel, a gun-operated apparatus, a saw, or the like, capable of creating an incision through osseous tissue to accomplish this function. In some embodiments, the bone cutting devices 106 may be coupled to the fixed portion 102 using spherical joints or hinge joints (not shown), so that the bone cutting devices 106 may be oriented and maintained along different axes or be mechanically configured with multiple degrees of freedom. In some embodiments, the bone cutting devices 106 may also be in linear sliding engagement along the fixed portion 102 (not shown). In some embodiments, the bone cutting devices 106 are configured so that cutting depths can be controlled; i.e., the surgeon may carefully control the depth of any incision into the bone tissue. Dimensions of the bone cutting devices 106 may also vary with respect to length and width as needed.

The apparatus 100 may enable surgeons to remove bone tissue safely and more efficiently. As one example, a neurosurgeon may employ the apparatus 100 to quickly and safely perform a laminectomy. Specifically, once a target vertebra has been exposed and is available for access, the clamp 104 of the apparatus 100 may be engaged to the spinous process 110 by driving the clamp legs 114 together and gripping the spinous process 110.

The surgeon may also align the bone cutting devices 106 along portions of the vertebra, and accurately position the bone cutting devices 106 over the lamina 112 in the position and angle desired. The bone cutting devices 106 may then be employed to form bilateral, controlled longitudinal incisions or cuts in order to remove the lamina 112 and/or the spinous process 110 from the vertebra 108. In the case where the bone cutting devices 106 include osteotomes, any force on the lamina 112 generated by application of the osteotomes is transmitted to the clamp 104, thereby canceling the force generated on the lamina 112 from the operation of the osteotomes so that the apparatus 100 remains in a stationary position relative to the vertebra 108 during the procedure.

Once incisions formed by the bone cutting devices 106 are advanced to a predefined appropriate depth, the lamina 112 may naturally release from the vertebra 108 and can be removed as a single piece with the spinous process 110 still attached to the clamp 104. Using the apparatus 100 as described, the dura mater surrounding the vertebra 108 underneath the lamina 112 is unlikely to be cut, and the laminectomy procedure is efficient and precise in its application. In this example, the laminectomy procedure may be completed within a time span of one to three minutes or less. The apparatus 100 may involve primarily inexpensive mechanical components as opposed to software or electromechanical components. Aspects of the apparatus 100 may be formed using surgical steel, although the present disclosure is not limited in this regard.

Figure 2:
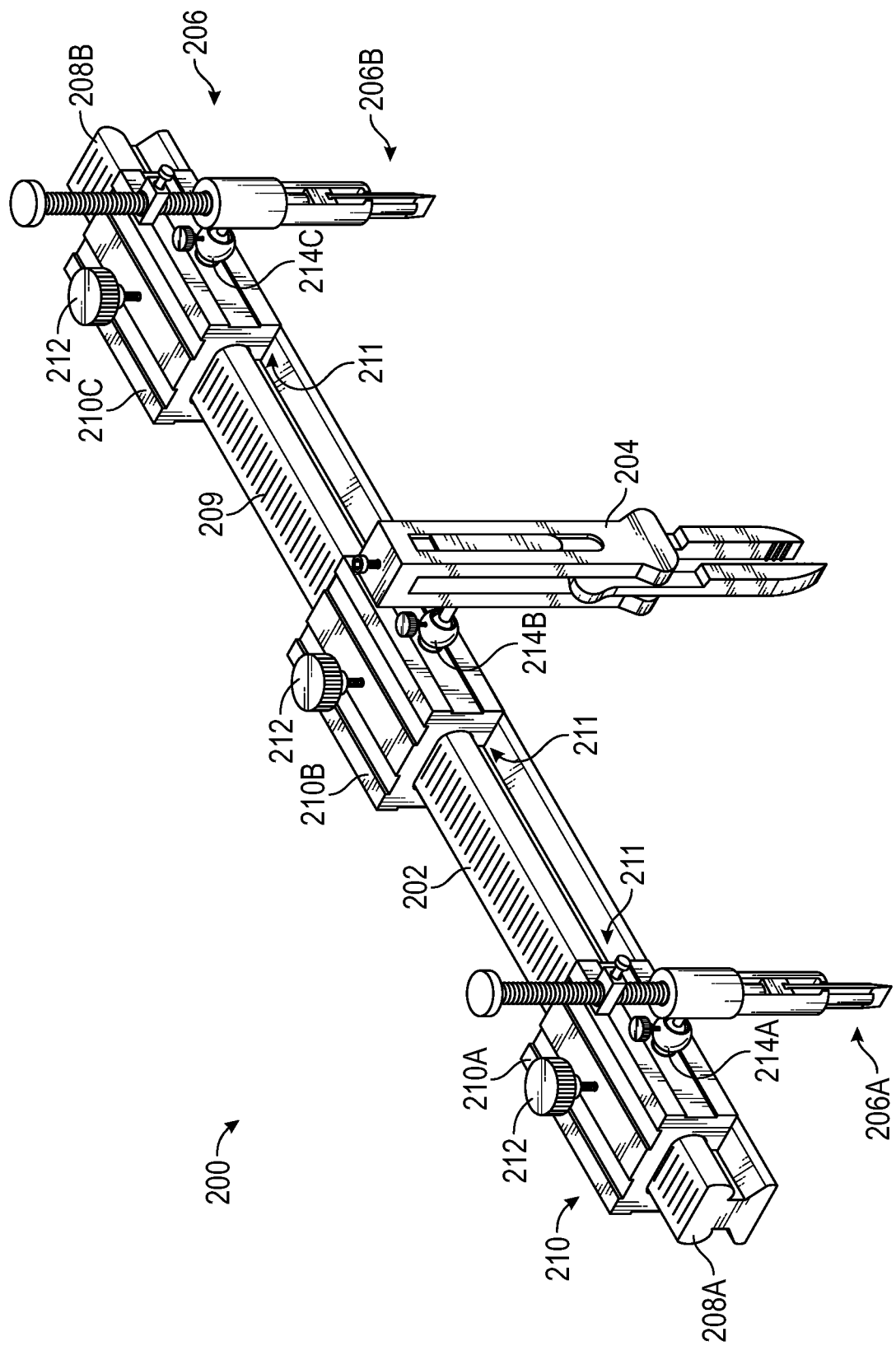
FIG. 2 is a perspective view of a first embodiment of an apparatus for removal and extraction of osseous tissue including a first embodiment of a bone cutting device, according to aspects of the present disclosure.
Figure 3:
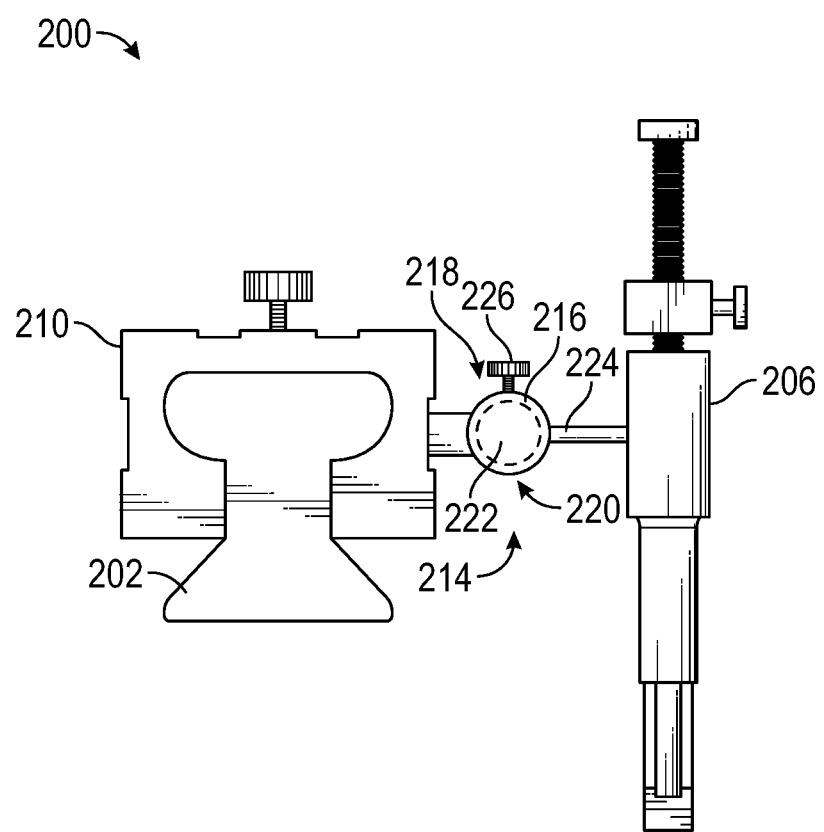
FIG. 3 is a side view of the apparatus of FIG. 2, according to aspects of the present disclosure.
Figure 4:
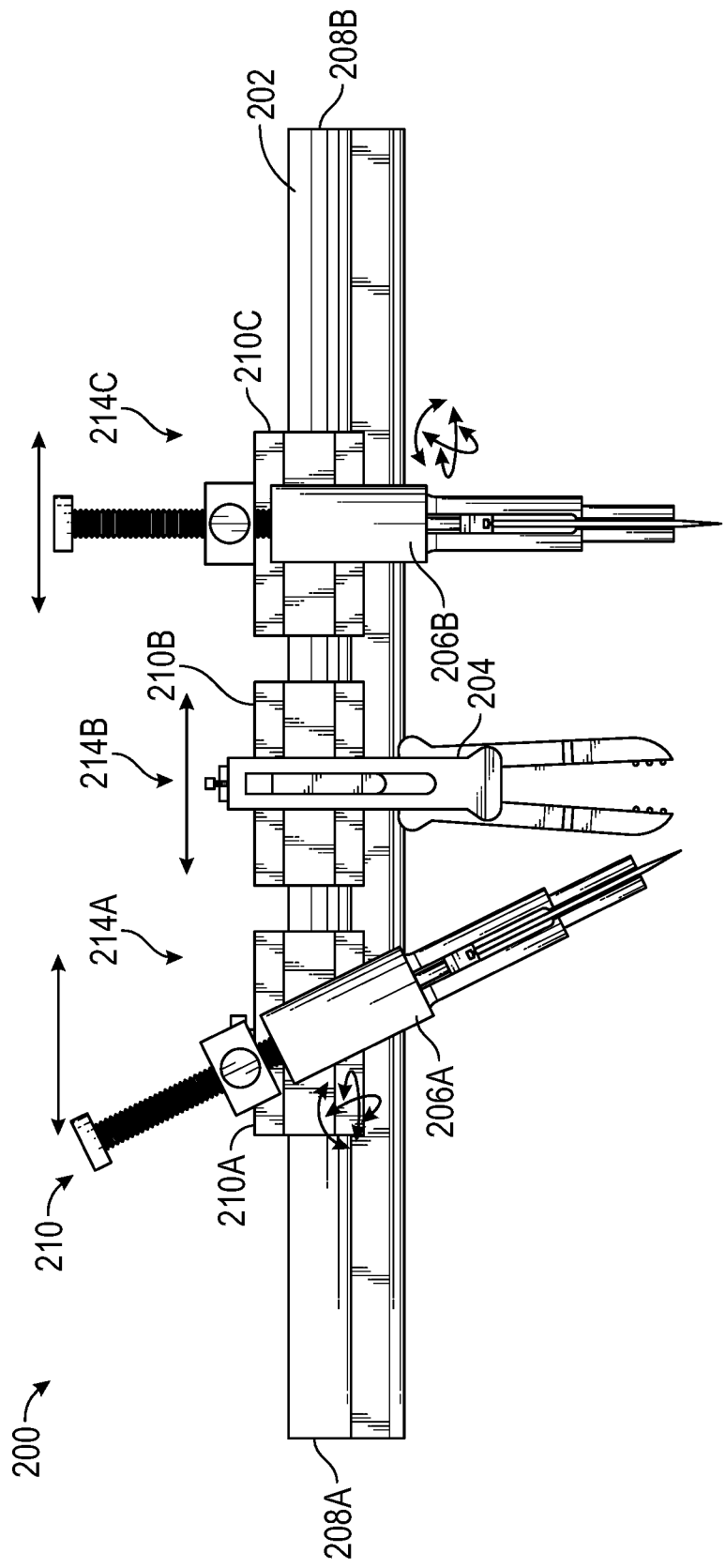
FIG. 4 is a front view that illustrates possible movements of a plurality of bone cutting devices and a clamp of the apparatus of FIG. 2 relative to a fixed portion, according to aspects of the present disclosure.

Referring to FIGS. 2-4, one embodiment of an apparatus, designated 200, includes a fixed portion 202, a clamp 204 coupled to a generally central position along the fixed portion 202, and a plurality of a first embodiment of bone cutting devices, defined as osteotomes 206 (and illustrated as osteotome 206A and osteotome 206B), that are coupled to the fixed portion 202 and oriented generally adjacent to the clamp 204, such that the clamp 204 is positioned between the osteotome 206A and the osteotome 206B. It should be understood that a pair of osteotomes 206 and a sole clamp 204 are shown solely for illustrating possible aspects of the present disclosure, and some embodiments may include a plurality of clamps, a sole osteotome, or more than two osteotomes as may be suitable for specific applications. The osteotomes 206 and clamp 204 are described in greater detail below, but the osteotomes 206 illustrate one possible implementation of bone cutting devices previously described in FIG. 1 that may be configured to form incisions within bone in order to accommodate removal of bone tissue, and the clamp 204 may be generally configured to grip other bone tissue during surgery.

In some embodiments, the fixed portion 202 comprises a substantially linear rail, and may be generally cuboidal in shape, i.e. define an elongated three-dimensional rectangle shape as shown (although cylindrical/rod shapes and other such shapes are contemplated in related embodiments). The fixed portion 202 may be generally configured to extend horizontally over a bone such as the vertebra 108 of a patient during a laminectomy, similar to the orientation of the fixed portion 102 of the apparatus 100 relative to the vertebra 108 shown in FIG. 1. The fixed portion 202 defines a first end 208A, and a second end 208B opposite the first end 208A. In some embodiments, the fixed portion 202 defines a plurality of markers 209 arranged along the length of the fixed portion 202. The plurality of markers 209 may define etchings, labels, indentations, or the like and may be associated with units of measurement to assist a surgeon with arranging the clamp 204 and the osteotomes 206 over predetermined positions along the fixed portion 202, as further described herein.

In some embodiments, a plurality of carriages 210 may be mechanically coupled to the fixed portion 202 of the apparatus 200. In the present embodiment shown, the plurality of carriages 210 may be illustrated as carriage 210A, carriage 210B, and carriage 210C. In some embodiments, the carriage 210A is positioned generally along the first end 208A, the carriage 210C is positioned generally along the second end 208B, and the carriage 210B is positioned between the carriage 210A and the carriage 210C. Each of the carriages 210 may be oriented in linear sliding engagement along the fixed portion 202. Specifically, as shown in FIG. 2, each of the carriages 210 may define a respective channel 211 extending through each of the carriages 210, and the carriages 210 may be slidably mounted along the fixed portion 202 by inserting either the first end 208A or the second end 208B of the fixed portion 202 through the channels 211 of the carriages 210. The plurality of carriages 210 may define linear bearings, slide casings, or linear/prismatic joints that are capable of linear sliding movement along the fixed portion 202, as further described herein. In some embodiments, as shown, the fixed portion 202 may be formed with linear guides or rails, and the channels 211 may be formed of a shape that is suitable for receiving the linear guides in order to movably mount and maintain the carriages 210 along the guide rails of the fixed portion 202, although the present disclosure is not limited in this regard.

In some embodiments, each of the carriages 210 may include a respective tightening knob 212 or other such locking mechanism for restricting linear movement of the carriages 210 along the fixed portion 202. In other words, when the tightening knob 212 of the carriage 210A is engaged, the tightening knob 212 maintains the carriage 210A in a locked or stationary position relative to the fixed portion 202. Maintaining the carriages 210 in a locked or stationary position relative to the fixed portion 202 may be advantageous during surgery when various forces may be exerted upon the apparatus 200, as further described herein.

As further shown, a plurality of spherical joints 214 may be mounted to or otherwise defined along the carriages 210. In particular, as illustrated, a spherical joint 214A may be included along the carriage 210A, a spherical joint 214B may be included along the carriage 210B, and a spherical joint 214C may be included along the carriage 210C. The spherical joints 214 may define ball joints, ball bearings, spherical bearings, ball and socket joints, or the like.

Referring to FIG. 3, in some embodiments, each of the spherical joints 214 may include at least a housing body 216 defining a cavity 218, with the housing body 216 mounted or otherwise defined along the carriage 210 of the apparatus 200. The spherical joints 214 may further include a ball stud 220 defining a ball portion 222 in communication with a stem portion 224. The ball portion 222 of the ball stud 220 may be rotatably engaged within the cavity 218 of the housing body 216 to accommodate angular rotation of the stem portion 224 relative to the housing body 216 and enable multiple degrees of freedom. Further, as shown, the stem portion 224 may be coupled to or mounted along an osteotome 206 (or the clamp 204 (not shown)). In this manner, the osteotome 206 may be oriented along different horizontal and vertical axes, and may be rotated relative to the fixed portion 202 by nature of the osteotome 206 being coupled to the spherical joint 214.

In some embodiments as shown, the spherical joints 214 may include a tightening knob 226 or other like locking mechanism similar to the tightening knobs 212 for restricting movement of the ball stud 220 relative to the housing body 216. In other words, when the tightening knob 226 of a spherical joint 214 is engaged, the tightening knob 226 maintains the ball stud 220 in a substantially locked or stationary position relative to the housing body 216 and restricts angular and rotational movement thereof. Maintaining the ball stud 220 in a locked or stationary position relative to the housing body 216 may be advantageous during surgery when various forces may be exerted upon the apparatus 200 and it is desired to maintain the osteotomes 206 (and/or the clamp 204) in a stationary position.

Referring to FIG. 4, each of the clamp 204, the osteotome 206A, and the osteotome 206B, when coupled to any one of the spherical joints 214, may be configured with multiple degrees of freedom, i.e., may be oriented along different horizontal and vertical axes relative to the fixed portion 202. In addition, by virtue of the spherical joints 214 being coupled to the carriages 210, the linear positioning of each of the clamp 204, the osteotome 206A, and the osteotome 206B along the fixed portion 202 may be adjusted by sliding the carriages 210 to different predetermined positions along the fixed portion 202 as desired. For example, as indicated by the horizontal arrows shown, the carriage 210A (and the osteotome 206A) may be advanced along the fixed portion 202 towards the first end 208A or the second end 208B to a predetermined position (not shown) as desired, and the tightening knob 212 of carriage 210A may be actuated, tightened or otherwise engaged to lock the carriage 210A or otherwise maintain the carriage 210A in a substantially stationary configuration along the predetermined position. In addition, with the spherical joint 214A provided along the carriage 210 as described, and the osteotome 206A being coupled to the spherical joint 214A, the osteotome 206A may be oriented along different horizontal and vertical axes relative to the fixed portion 202 (as illustrated by the curved arrows), independently of the osteotome 206B and the clamp 204. The clamp 204, when coupled to the spherical joint 214B and the carriage 210B, and the osteotome 206B, when coupled to the spherical joint 214C and the carriage 210C, are capable of the same or similar movement. Once the components of the apparatus 200 (the clamp 204, the osteotome 206A, and the osteotome 206B) are oriented as desired, the surgeon may engage the tightening knobs 212 and the tightening knobs 226 (FIG. 3) to temporarily maintain these orientations during a surgical procedure. This enhanced flexibility, maneuverability, and stability of the apparatus 200 components may allow a surgeon to more accurately align the apparatus 200 along a vertebra or other bone tissue and safely complete a cutting procedure.

Figure 5A:
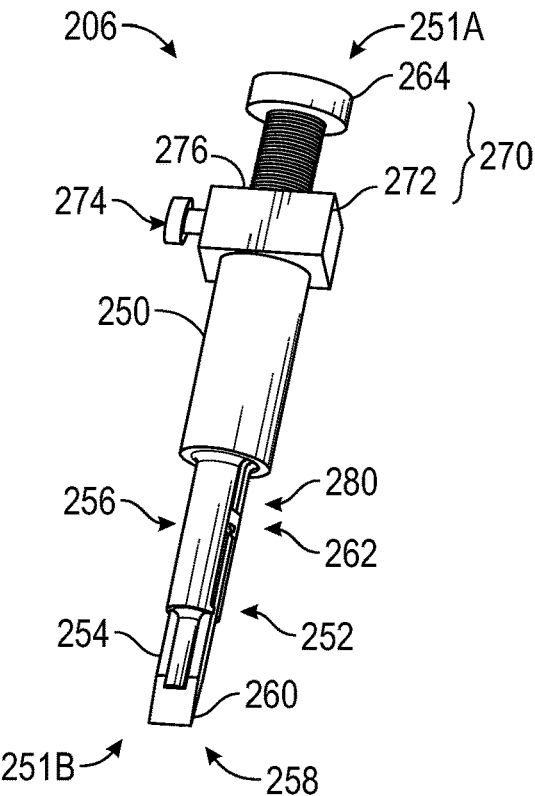
FIGS. 5A-5B are perspective views of the first embodiment of the bone cutting device shown in FIGS. 2-4 with portions of FIG. 5B cut-away for illustration, according to aspects of the present disclosure.
Figure 5B:
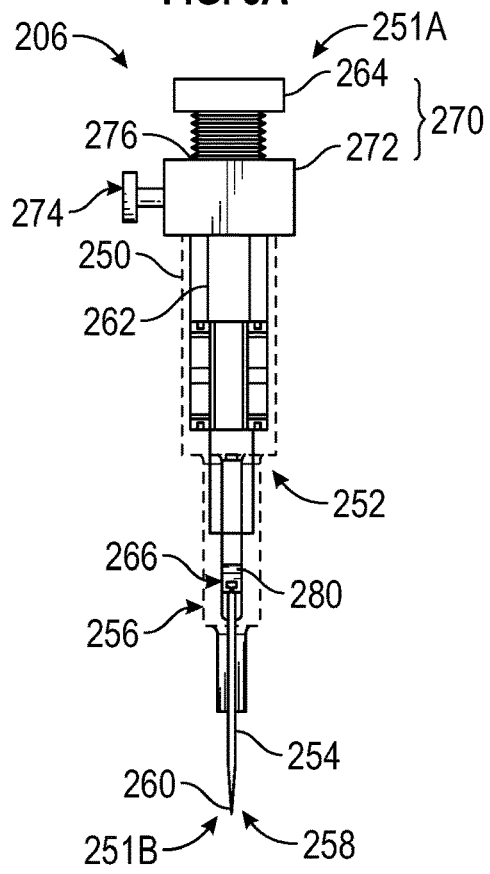
Figure 5C:
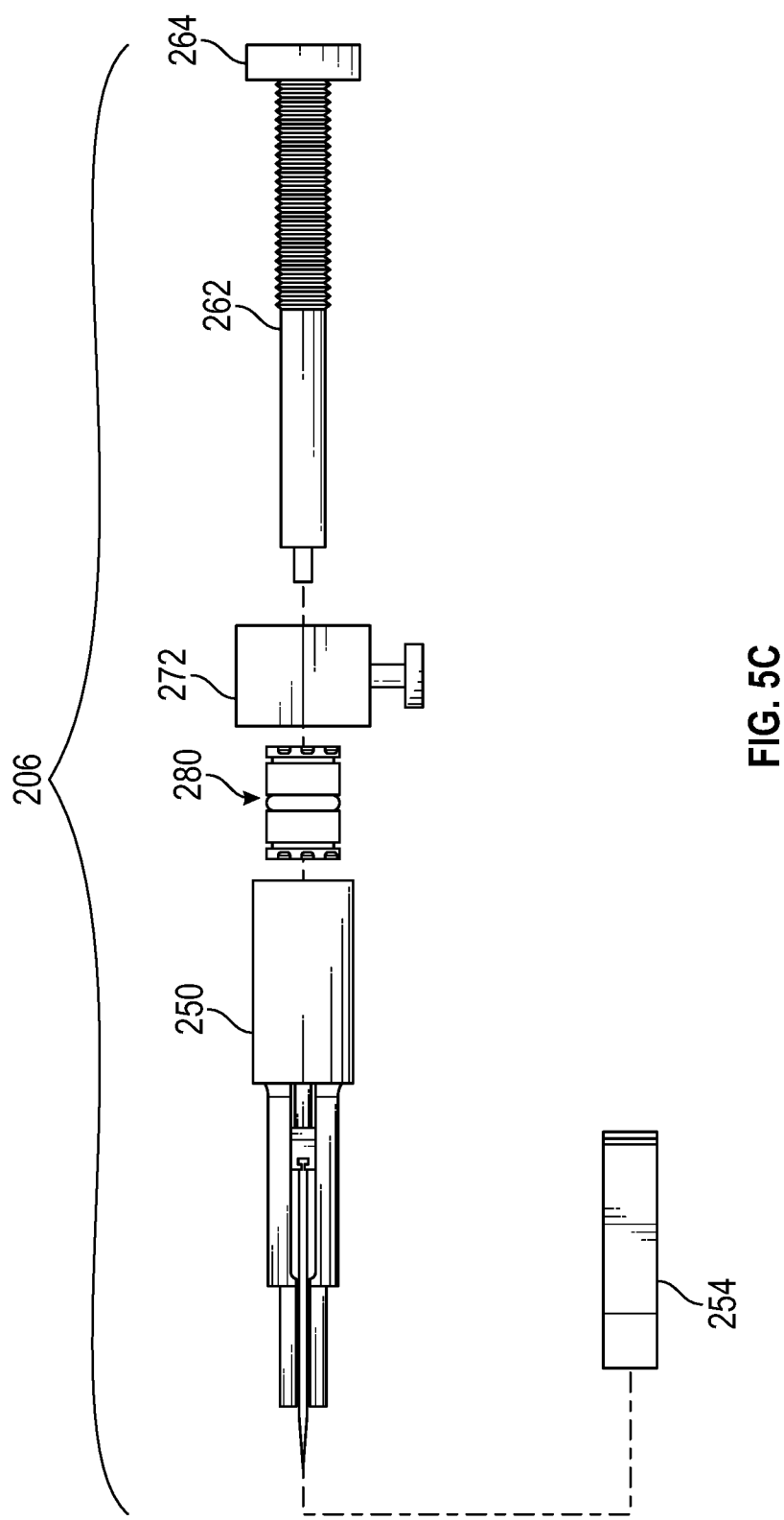
FIG. 5C is an exploded view of the first embodiment of the bone cutting device shown in FIGS. 2-4, according to aspects of the present disclosure.

Referring to FIGS. 5A-5C, the osteotomes 206 are generally configured for controlled reciprocating motion to drive a blade into bone tissue and form precise cuts along the same, and the osteotomes 206 may include a stopping mechanism for adjusting the depth of cuts formed by the blade, as described herein. Accordingly, in some embodiments an osteotome 206 as shown may include a body 250 defining a proximal end 251A and a distal end 251B with a channel 252 extending longitudinally at least partially through the body 250 between the proximal end 251A and the distal end 251B. A blade 254 may be positioned within the channel 252 of the body 250. The blade 254 may include a proximal end 256 and a distal end 258 where the distal end 258 of the blade 254 defines a cutting portion 260. The blade 254 may be configured to slidably shift up and down along the channel 252 in a controlled manner as further described herein.

In some embodiments, as shown, the blade 254 may be coupled to a rod 262. The rod 262 may be at least partially engaged within the channel 252 of the body 250 and may define a head portion 264 and a rod-blade interface 266 (FIG. 5C) defined along the rod 262 opposite the head portion 264. In addition, the rod 262 may include a threaded portion (not shown).

The osteotome 206 may further include a stopping mechanism 270 for restricting the depth of cuts formed by the blade 254. In the embodiment shown, the stopping mechanism 270 defines a quick quill stop 272 engaged along the rod 262 as shown. The quick quill stop 272 may include an adjustment knob 274 defined along a periphery of the adjustment knob 274, and a stopping surface 276 oriented towards the head portion 264. The quick quill stop 272 may be internally threaded to engage with a threaded portion (not shown) of the rod 262 in order to accommodate linear controller movement of the quick quill stop 272 along the rod 262, using the adjustment knob 274. The quick quill stop 272 enables a user to present the depth of the cuts formed by the blade 254. Specifically, where a force is applied to the head portion 264 of the rod 262, the stopping surface 276 of the quick quill stop 272 impacts the head portion 264 as the force drives the rod 262 and the blade 254 towards the distal end 251B of the body 250, thereby limiting the depth of any cut formed by the blade 254.

In some embodiments, the osteotome 206 may further include a linear ball bearing 280 oriented along the channel 252 of the body 250 as shown. A portion of the rod 262 and blade 254 may be engaged to the linear ball bearing 280 to reduce friction and accommodate linear sliding engagement of the rod 262 and blade 254 through the channel 252. In some embodiments, at least a portion of the body 250 is configured to be embedded within bone tissue during cut formation.

Figure 6:
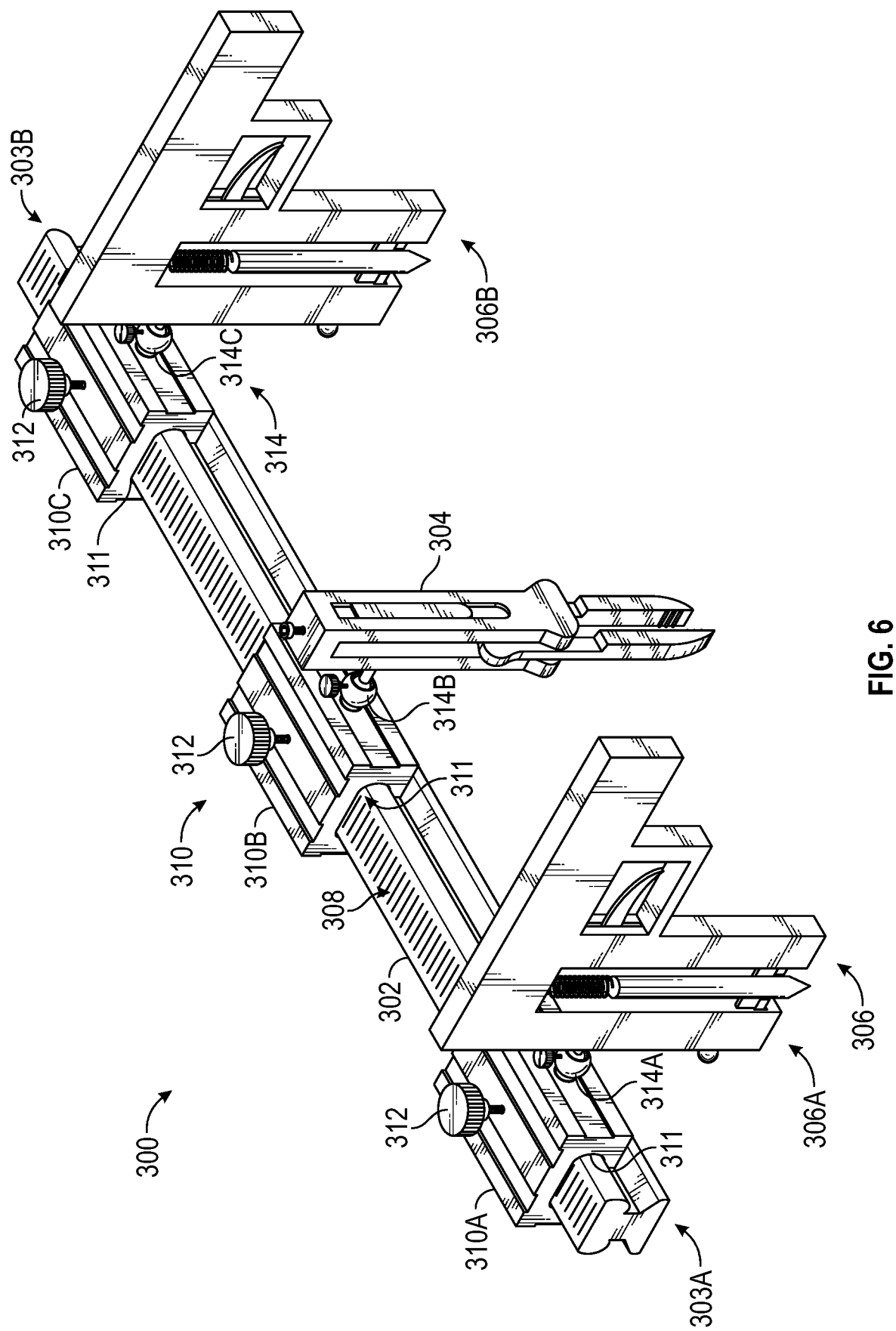
FIG. 6 is a perspective view of a second embodiment of an apparatus for removal and extraction of osseous tissue including a second embodiment of a bone cutting device, according to aspects of the present disclosure.

Referring to FIG. 6, a second embodiment of an apparatus, designated 300, includes a fixed portion 302, a clamp 304 coupled to a generally central position along the fixed portion 302, and a plurality of a second embodiment of bone cutting devices or osteotomes 306, illustrated as osteotome 306A and osteotome 306B, that are coupled to the fixed portion 302 and oriented generally adjacent to the clamp 304, such that the clamp 304 is positioned between the osteotome 306A and the osteotome 306B. It should be understood that a pair of osteotomes 306 and a sole clamp 304 are shown solely for illustrating possible aspects of the present disclosure, and some embodiments may include a plurality of clamps, a sole osteotome, or more than two osteotomes as may be suitable for specific applications.

In some embodiments, the fixed portion 302 comprises a substantially linear rail, and may be generally cuboidal in shape, i.e. define an elongated three-dimensional rectangle shape as shown (although cylindrical/rod shapes and other such shapes are contemplated in related embodiments). The fixed portion 302 may be generally configured to extend horizontally over a bone such as a vertebra of a patient during a laminectomy. The fixed portion 302 defines a first end 303A, and a second end 303B opposite the first end 303A. In some embodiments, the fixed portion 302 defines a plurality of markers 308 arranged along the length of the fixed portion 302. The plurality of markers 308 may define etchings, labels, indentations, or the like and may be associated with units of measurement to assist a surgeon with arranging the clamp 304 and the osteotomes 306 over predetermined positions along the fixed portion 302, as further described herein.

In some embodiments, a plurality of carriages 310 may be mechanically coupled to the fixed portion 302 of the apparatus 300. In the present embodiment shown, the plurality of carriages 310 may be illustrated as carriage 310A, carriage 310B, and carriage 310C. In some embodiments, the carriage 310A is positioned generally along the first end 303A, the carriage 310C is positioned generally along the second end 303B, and the carriage 310B is positioned between the carriage 310A and the carriage 310C. Each of the carriages 310 may be oriented in linear sliding engagement along the fixed portion 302. Specifically, each of the carriages 310 may define a respective channel 311 extending through each of the carriages 310, and the carriages 310 may be slidably mounted along the fixed portion 302 by inserting either the first end 303A or the second end 303B of the fixed portion 302 through the channels 311 of the carriages 310. The plurality of carriages 310 may define linear bearings, slide casings, or linear/prismatic joints that are capable of linear sliding movement along the fixed portion 302, as further described herein. In some embodiments, as shown, the fixed portion 302 may be formed with linear guides or rails, and the channels 311 may be formed of a shape that is suitable for receiving the linear guides in order to movably mount and maintain the carriages 310 along the guide rails of the fixed portion 302, although the present disclosure is not limited in this regard.

In some embodiments, each of the carriages 310 may include a respective tightening knob 312 or other such locking mechanism for restricting linear movement of the carriages 310 along the fixed portion 302. In other words, when the tightening knob 312 of the carriage 310A is engaged, the tightening knob 312 maintains the carriage 310A in a locked or stationary position relative to the fixed portion 302. Maintaining the carriages 310 in a locked or stationary position relative to the fixed portion 302 may be advantageous during surgery when various forces may be exerted upon the apparatus 300, as further described herein.

As further shown, a plurality of spherical joints 314 may be mounted to or otherwise defined along the carriages 310. In particular, as illustrated, a spherical joint 314A may be included along the carriage 310A, a spherical joint 314B may be included along the carriage 310B, and a spherical joint 314C may be included along the carriage 310C. The spherical joints 314 may define ball joints, ball bearings, spherical bearings, ball and socket joints, or the like.

Figure 7:
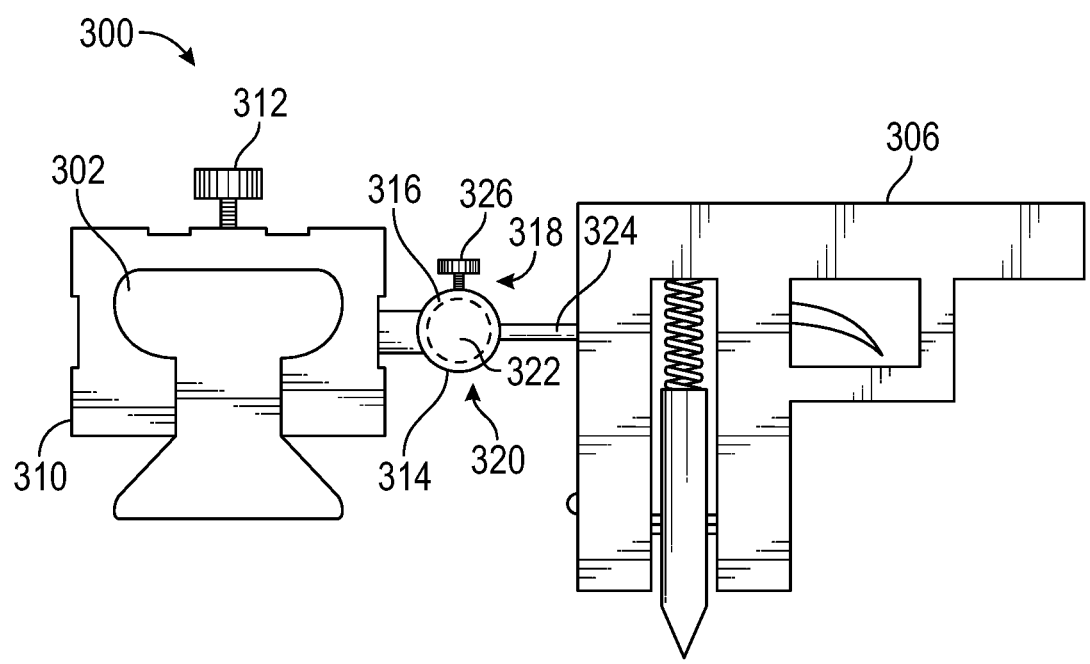
FIG. 7 is a side view of the apparatus of FIG. 6, according to aspects of the present disclosure.

Referring to FIG. 7, in some embodiments, each of the spherical joints 314 may include at least a housing body 316 defining a cavity 318, with the housing body 316 mounted or otherwise defined along the carriage 310 of the apparatus 300. The spherical joints 314 may further include a ball stud 320 defining a ball portion 322 in communication with a stem portion 324. The ball portion 322 of the ball stud 320 may be rotatably engaged within the cavity 318 of the housing body 316 to accommodate angular rotation of the stem portion 324 relative to the housing body 316 and enable multiple degrees of freedom. Further, as shown, the stem portion 324 may be coupled to or mounted along an osteotome 306 (or the clamp 304 (not shown)). In this manner, the osteotome 306 may be oriented along different horizontal and vertical axes, and may be rotated relative to the fixed portion 302 by nature of the osteotome 306 being coupled to the spherical joint 314.

In some embodiments as shown, the spherical joints 314 may include a tightening knob 326 or other like locking mechanism similar to the tightening knobs 312 for restricting movement of the ball stud 320 relative to the housing body 316. In other words, when the tightening knob 326 of a spherical joint 314 is engaged, the tightening knob 326 maintains the ball stud 320 in a substantially locked or stationary position relative to the housing body 316 and restricts angular and rotational movement thereof. Maintaining the ball stud 320 in a locked or stationary position relative to the housing body 316 may be advantageous during surgery when various forces may be exerted upon the apparatus 300 and it is desired to maintain the osteotomes 306 (and/or the clamp 304) in a stationary position.

Figure 8:
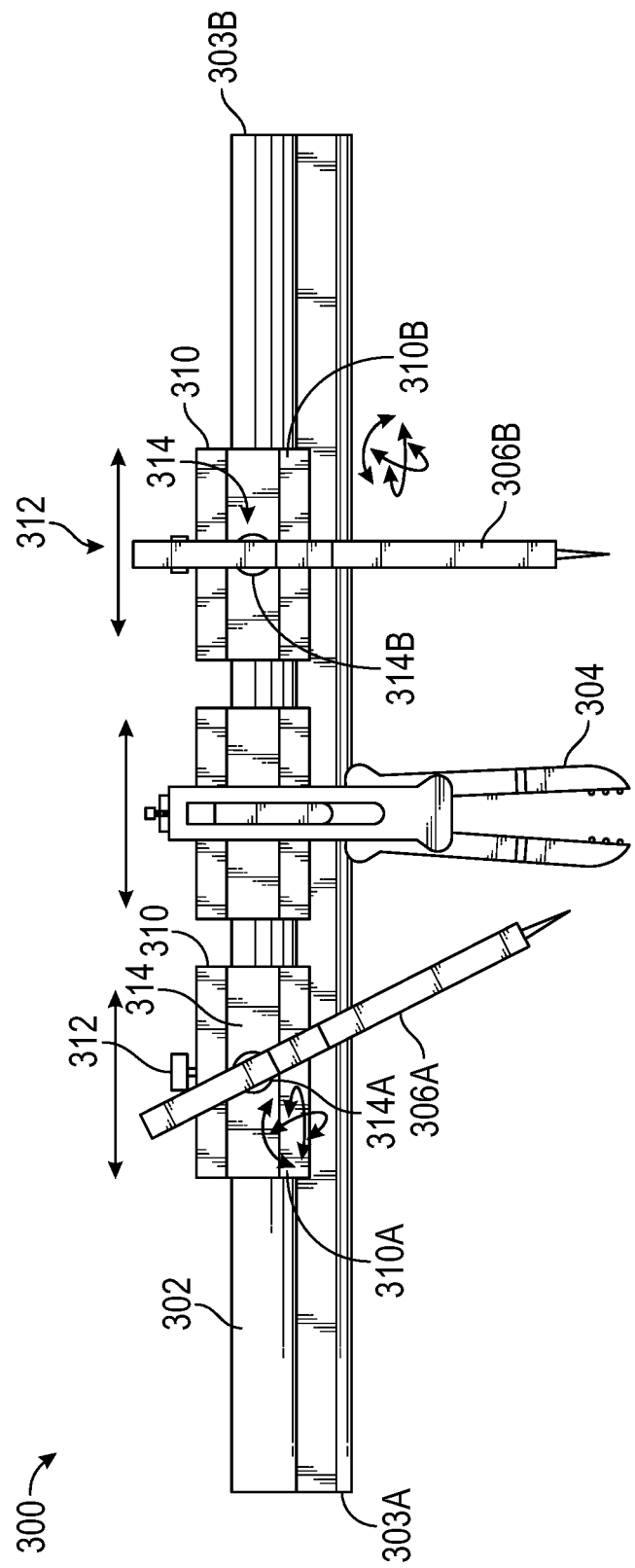
FIG. 8 is a front view that illustrates possible movements of a plurality of bone cutting devices and a clamp of the apparatus of FIG. 6 relative to a fixed portion, according to aspects of the present disclosure.

Referring to FIG. 8, each of the clamp 304, the osteotome 306A, and the osteotome 306B, when coupled to any one of the spherical joints 314, may be configured with multiple degrees of freedom, i.e., may be oriented along different horizontal and vertical axes relative to the fixed portion 302. In addition, by virtue of the spherical joints 314 being coupled to the carriages 310, the linear positioning of each of the clamp 304, the osteotome 306A, and the osteotome 306B along the fixed portion 302 may be adjusted by sliding the carriages 310 to different predetermined positions along the fixed portion 302 as desired. For example, as indicated by the horizontal arrows of FIG. 8, the carriage 310A (and the osteotome 306A) may be advanced along the fixed portion 302 towards the first end 303A or the second end 303B to a predetermined position (not shown) as desired, and the tightening knob 312 defined along the carriage 310A may be actuated, tightened or otherwise engaged to lock the carriage 310A or otherwise maintain the carriage 310A in a substantially stationary configuration along the predetermined position. In addition, with the spherical joint 314A defined along the carriage 310 as described, and the osteotome 306A being coupled to the spherical joint 314A, the osteotome 306A may be oriented along different horizontal and vertical axes relative to the fixed portion 302 (as illustrated by the curved arrows), independently of the osteotome 306B and the clamp 304. The clamp 304, when coupled to the spherical joint 314B and the carriage 310B, and the osteotome 306B, when coupled to the spherical joint 314C (FIG. 6) and the carriage 310C, are capable of the same or similar movement. Once the components of the apparatus 300 (the clamp 304, the osteotome 306A, and the osteotome 306B) are oriented as desired, the surgeon may engage the tightening knobs 312 and the tightening knobs 326 (FIG. 6) to temporarily maintain these orientations during a surgical procedure. This enhanced flexibility, maneuverability, and stability of the apparatus 300 components may allow a surgeon to more accurately align the apparatus 300 along a vertebra or other bone tissue and safely complete a cutting procedure.

Figure 9:
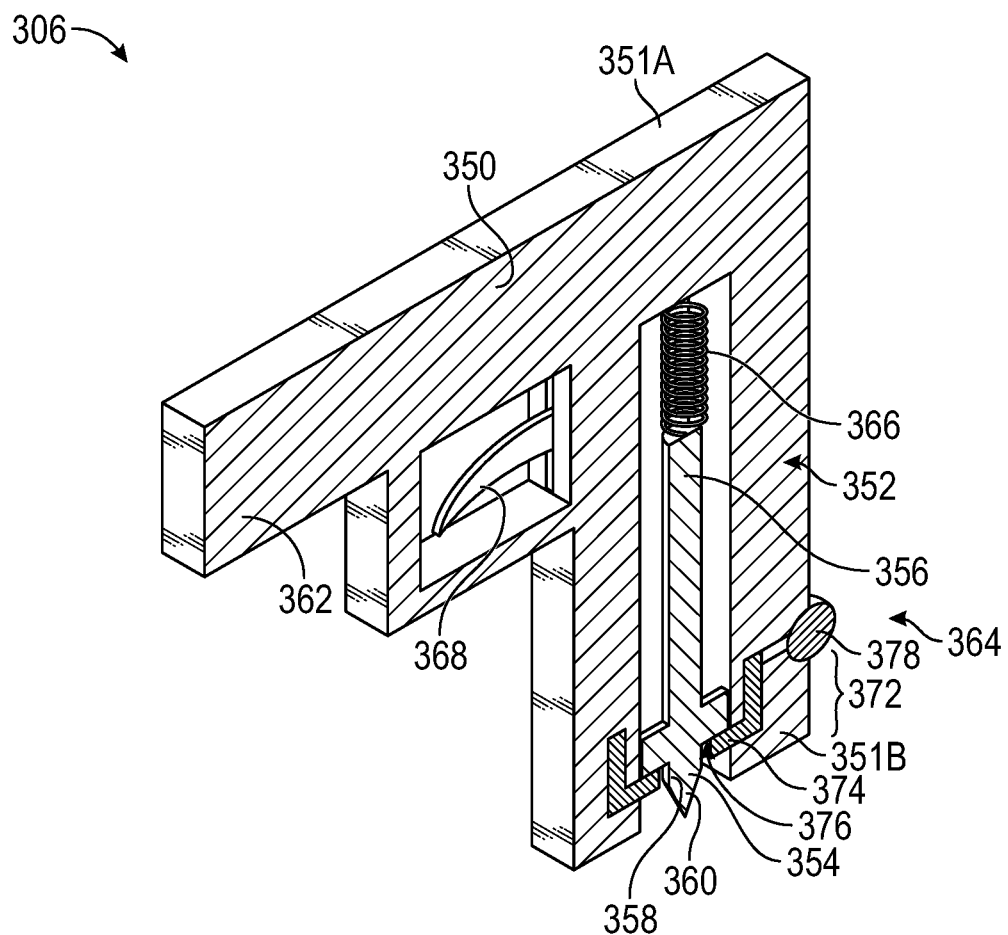
FIG. 9 is a cross-sectional view of the second embodiment of a bone cutting device as shown in FIGS. 6-8, according to aspects of the present disclosure.

Referring to FIG. 9, the osteotomes 306 are generally configured for driving a blade into bone tissue and making predetermined controlled cuts, and includes a stopping mechanism for adjusting the depth of cuts formed by the blade, as described herein. Accordingly, in some embodiments an osteotome 306 as shown may include a body 350, defining a proximal end 351A and a distal end 351B, with a channel 352 extending longitudinally at least partially through the body 350. A blade 354 may be slidably engaged within the channel 352 of the body 350. The blade 354 may include a proximal end 356 and a distal end 358 where the distal end 358 of the blade 354 defines a cutting portion 360.

In this embodiment, the osteotome 306 is generally configured to have the shape of gun, and may also include similar functionality. In particular, the body 350 may define a handle 362 along the proximal end 351A which may be configured to accommodate the shape of a surgeons hand for increased stability during formation of a cut with the blade 354, as further described herein. Further, a barrel 364 may be defined along the distal end 351B of the body 350. A spring 366 may be positioned within the channel 352 and engaged to the blade 354 such that the blade 354 is spring-loaded within the channel 352 of the body 350. In this manner, a trigger 368 may be included along the body 350 and be configured for releasing the spring 366 in order to launch the cutting portion 360 of the blade 354 away from the proximal end 351A of the body 350.

In some embodiments, the osteotome 306 may further include a ratchet (not shown) defined within the body 350. The ratchet may facilitate the gun to function similarly to a staple gun. For example, engaging the trigger 368 may allow the cutting portion 360 of the blade 354 of the osteotome 306 to be driven incrementally further, with each trigger 368 pull, along the channel 352 towards the distal end 351B.

As further shown, the osteotome 306 may include a stopping mechanism 372 for restricting the depth of cuts formed by the blade 354. In the embodiment shown, the stopping mechanism 372 includes a member 374 extending horizontally partially through the channel 352 as shown. The stopping mechanism 372 may further define a stopping edge 376 defined along the blade 354 configured to impact the member 374 in order to restrict cutting depth. The member 374 may be mechanically engaged to a knob 378, and manipulating the knob 378 may shift the member 374 along the channel 352, thereby restricting the cutting depth. In other words, by engaging the knob 378, the member 374 may be shifted towards (decrease cutting depth) or away (increase cutting depth) from the proximal end 351A of the osteotome 306.

In some embodiments, the osteotome 306 may further include a linear ball bearing (not shown) oriented along the channel 352 of the body 350 to reduce friction and accommodate linear sliding engagement of the blade 354 through the channel 352.

Figure 10:
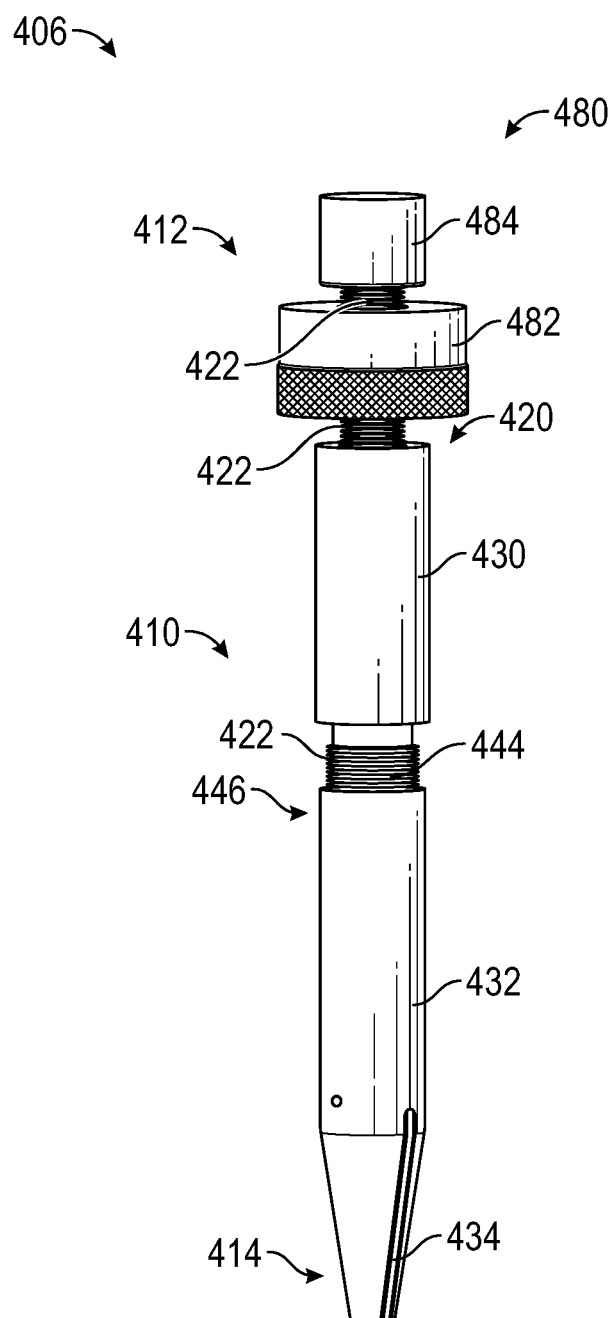
FIG. 10 is a side view of a third embodiment of a bone cutting device, according to aspects of the present disclosure.
Figure 11:
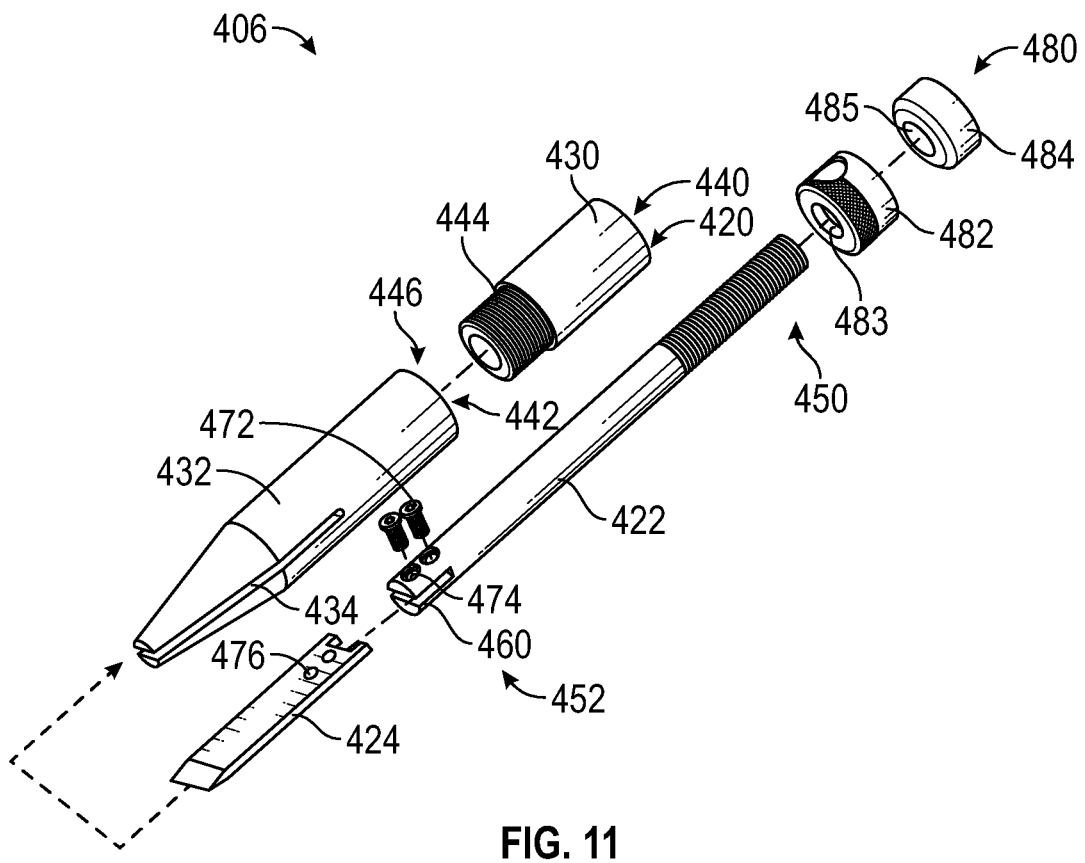
FIG. 11 is an exploded view of the third embodiment of a bone cutting device, according to aspects of the present disclosure.

Referring to FIGS. 10-11, another embodiment of a bone cutting device may take the form of an osteotome 406. In this embodiment, the osteotome 406 generally includes a body 410 defining a proximal end 412 and a distal end 414 with a channel 420 extending longitudinally at least partially through the body 410 between the proximal end 412 and the distal end 414. The osteotome 406 may further generally include a rod 422 slidably received within the channel 420 and a blade 424 (shown in FIG. 11) engaged to the rod 422 for forming incisions in or otherwise removing matter from bone tissue, as further described herein.

As further shown, in some embodiments, the body 410 includes an upper portion 430 defined along the proximal end 412, and a lower portion 432 defined along the distal end 414 with the lower portion 432 having a slot 434 defined therein to accommodate controlled linear movement of the blade 424 within the slot 434 relative to the lower portion 432 as further described herein. The slot 434 may extend from the distal end 414 at least partially through the lower portion 432 as indicated. In addition, the upper portion 430 of the body 410 may define a channel 440, and the lower portion 432 of the body 410 may define a channel 442 in communication with the slot 434. As further described herein, when the upper portion 430 of the body 410 is engaged with the lower portion 432, the channel 440 and the channel 442 linearly align and collectively form the channel 420, such that the channel 420 extends longitudinally entirely through the upper portion 430 and at least partially longitudinally through the lower portion 432. The upper portion 430 may be removably engaged to the lower portion 432. In one embodiment, for example, the upper portion 430 may define a plurality of external threads 444 axially arranged at least partially along the upper portion 430 as shown, and configured to engage with respective internal threads 446 defined within the lower portion 432 such that the upper portion 430 can be temporarily screwed onto the lower portion 432 or vice versa.

In some embodiments, the rod 422 may define a head portion 450 positioned proximate to the proximal end 412 of the body 410 and a rod-blade interface 452 defined along the rod 422 opposite the head portion 450 for engaging with the blade 424. As indicated, the rod-blade interface 452 of the osteotome 406 may include a slit 460 for receiving a portion of the blade 424. To assemble the osteotome 406, the upper portion 430 of the body 410 may be connected to the lower portion 432 as described, the rod-blade interface 452 may be oriented towards the upper portion 430, the rod 422 may be inserted within the channel 440 and positioned within the channel 420, and the rod 422 may extend through the channel 440 such that the rod-blade interface 452 is at least partially housed within the channel 442 and accessible via the slot 434. Upon positioning the rod 422 within the channel 420 as indicated, the blade 424 may then be inserted or otherwise received within the slot 434, and a portion of the blade 424 may be received within the slit 460 as indicated. Once the blade 424 is positioned within the slit 460, a plurality of securing members 472 (e.g., screws or the like) may be passed through apertures 474 defined within the rod-blade interface 452 and respective apertures 476 of the blade 424 to fasten the blade 424 to the rod 422 along the rod-blade interface 452. In this manner, the rod 422 is mechanically engaged to the blade 424, the rod 422 is in linear sliding engagement through the channel 420 of the body 410, and the blade 424 is in linear sliding engagement through the slot 434 of the lower portion 432 of the body 410. In some embodiments, dimensions of the blade 424, the channel 442, and/or the slot 434 may be preconfigured to restrict at least some degree of linear movement of the blade 424 through the channel 420 of the body 410 in a direction towards the upper portion 430. For example, the diameter of the channel 442 of the lower portion 432 may be narrower than the width of the blade 424. In these embodiments, once assembled as described, the rod 422 of the osteotome 406 may be prevented from simply sliding out of the channel 420 at the proximal end 412.

In some embodiments, the osteotome 406 further includes a stopping mechanism 480 for presetting or restricting the depth of cuts formed by the blade 424. In the embodiment shown, the stopping mechanism 480 includes a quick quill stop 482 defining a channel 483, and a head 484 defining a channel 485. The rod 422 may be threaded through the channel 483 of the quick quill stop 482 and at least partially threaded through the channel 485 of the head 484 in the manner shown, such that the quick quill stop 482 is in a predetermined position along the rod 422 in between the upper portion 430 of the body 410 and the head 484. In general, the quick quill stop 482 restricts linear movement of the rod 422 through the channel 420 and corresponding movement of the blade 424 relative to the slot 434 to control cutting depth when a blunt force is applied to the head 484 by a mallet or other such component.

Figure 12:
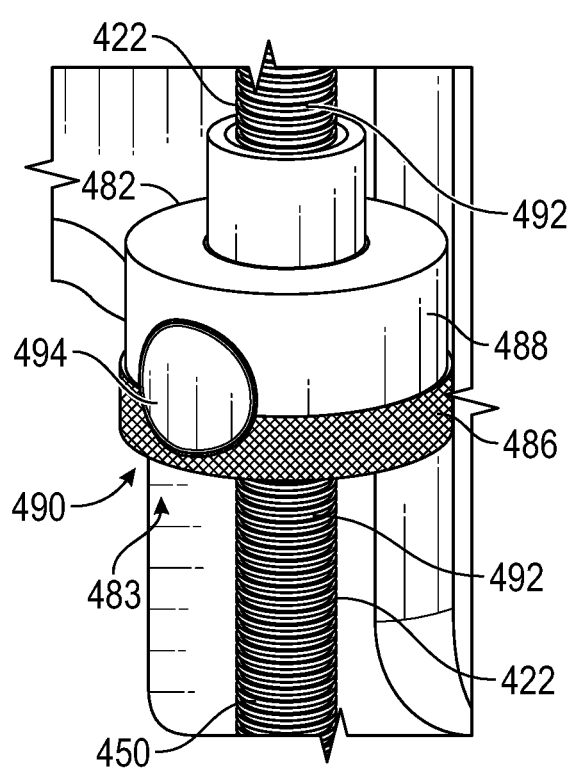
FIG. 12 is an enhanced view of the quick quill stop which may be implemented with the third embodiment of a bone cutting device, according to aspects of the present disclosure.

Referring to FIG. 12, the quick quill stop 482 generally includes a nut 486 rotatably engaged to a base 488. The nut 486 may define a plurality of threads 490 which engage with respective threads 492 defined along the head portion 450 of the rod 422. In some embodiments, the nut 486 further includes a button 494 that disengages the plurality of threads 490 from the respective threads 492 of the rod 422. To adjust linear movement of the quick quill stop 482 along the rod 422 relative to the head 484, a user may press the button 494 to disengage the plurality of threads 490 from the respective threads 492 of the rod 422 such that the quick quill stop 482 may slide along the rod 422 to a predetermined position along the rod 422 as desired, and releasing the button 494 may then re-engage the plurality of threads 490 with the respective threads 492 of the rod 422 to lock the quick quill stop 482 in the predetermined position. Alternatively, rotating the nut 486 provides gradual linear movement of the quick quill stop 482 along the rod 422 relative to the head 484 and the upper portion 430 by micro-adjustment (e.g., 0.001" increments). The quick quill stop 482 may be a quill stop for a Bridgeport Milling Machine, such as the Quill Stop by Morton Machine Works, or a Quick Thread Stop Collar or the Quick Quill Stop by Grizzly Industrial®, or the like, but the present disclosure is not limited in this regard.

Figure 13D:
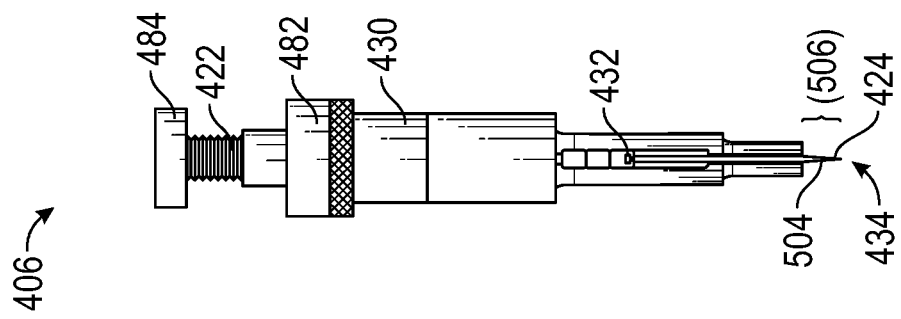
FIGS. 13A-13D are side views of the third embodiment of the bone cutting device shown in FIG. 10 illustrating a sequence for presetting a depth of a cut and applying a cut based on the desired depth, according to aspects of the present disclosure.
Figure 13C:
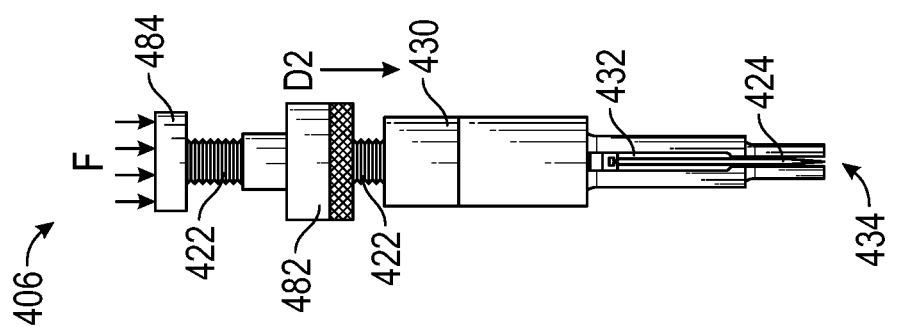
Figure 13B:
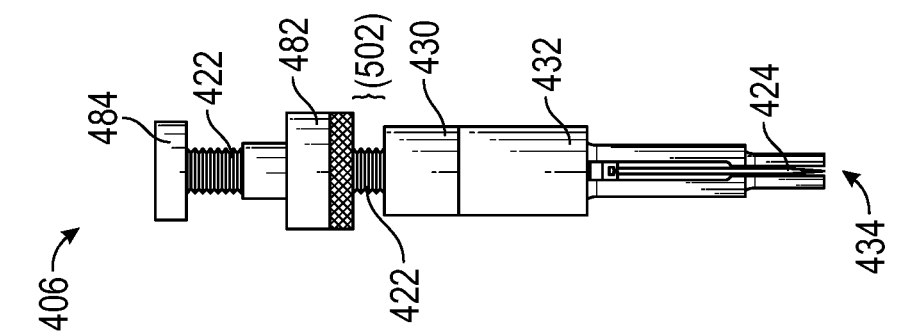
Figure 13A:
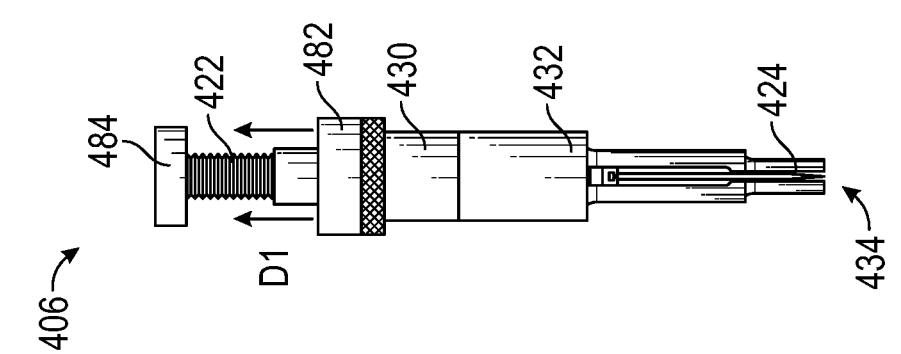

Referring to FIGS. 13A-13D, the quick quill stop 482 enables a user to preset the depth of the cuts formed by the blade 424 by restricting linear movement of the rod 422 through the channel 420. FIGS. 13A and 13B illustrate predetermined linear movement of the quick quill stop 482 in a direction D1 along the rod 422 to define a preset cutting depth 502 (although it should be understood that the quick quill stop 482 may be adjusted along the rod 422 in the opposite direction as desired to define the preset cutting depth 502).

FIG. 13C illustrates a force F applied to the head 484 (by a mallet or other such instrument), which results in at least some linear movement of the rod 422 in a direction D2 opposite the direction D1 through the channel 420 relative to the body 410 and at least some linear movement of the blade 424 relative to the slot 434 in the direction D2. As shown in FIG. 13D, the quick quill stop 482 impacts the upper portion 430 and is prevented from further linear movement, which in turns restricts movement of the rod 422 within the channel 420. A tip 504 of the blade extends outside the slot 434 of the lower portion 432 to form a cut with a cutting depth 506 equal to the preset cutting depth 502. Again, the contact between the quick quill stop 482 and the upper portion 430 of the body 410 limits the extension of the blade 424 through the slot 434 despite the force F applied to the head 484 to limit the cutting depth 506 (based on the value of the preset cutting depth 502).

The embodiment of the osteotome 406 shown provides various advantages. The lower portion 432 of the body 410 may be tapered as shown to increase yield strength without sacrificing visibility and also to provide a larger range of cutting alignment of the blade 424. The combination of the slit 460 of the rod 422 and the slot 434 of the lower portion 432 of the body 410 reduces lateral movement when the blade 424 is being used for leverage and/or prying. The slit 460 of the rod 422 is formed to a depth in which it promotes deflection when the securing members 472 are fastened, increasing the holding power and accommodating a secure/ tight fit. Embodiments of the osteotome 406 may generally comprise stainless steel, biocompatible materials, or combinations thereof.

Figure 14:
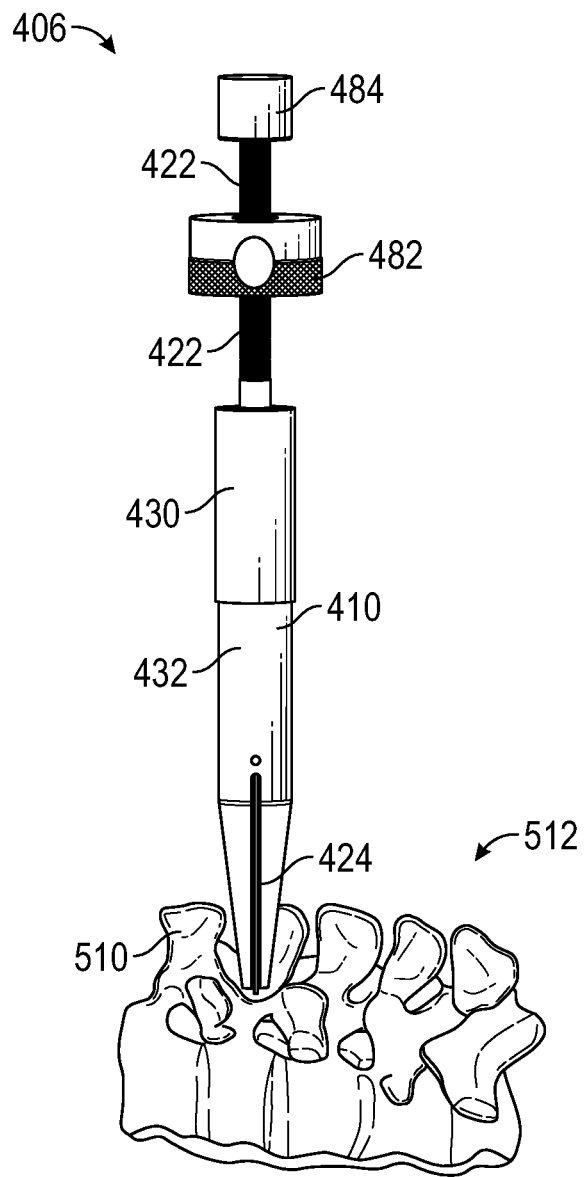
FIG. 14 is a side anatomical view of a third embodiment of a bone cutting device, according to aspects of the present disclosure.
Figure 15:
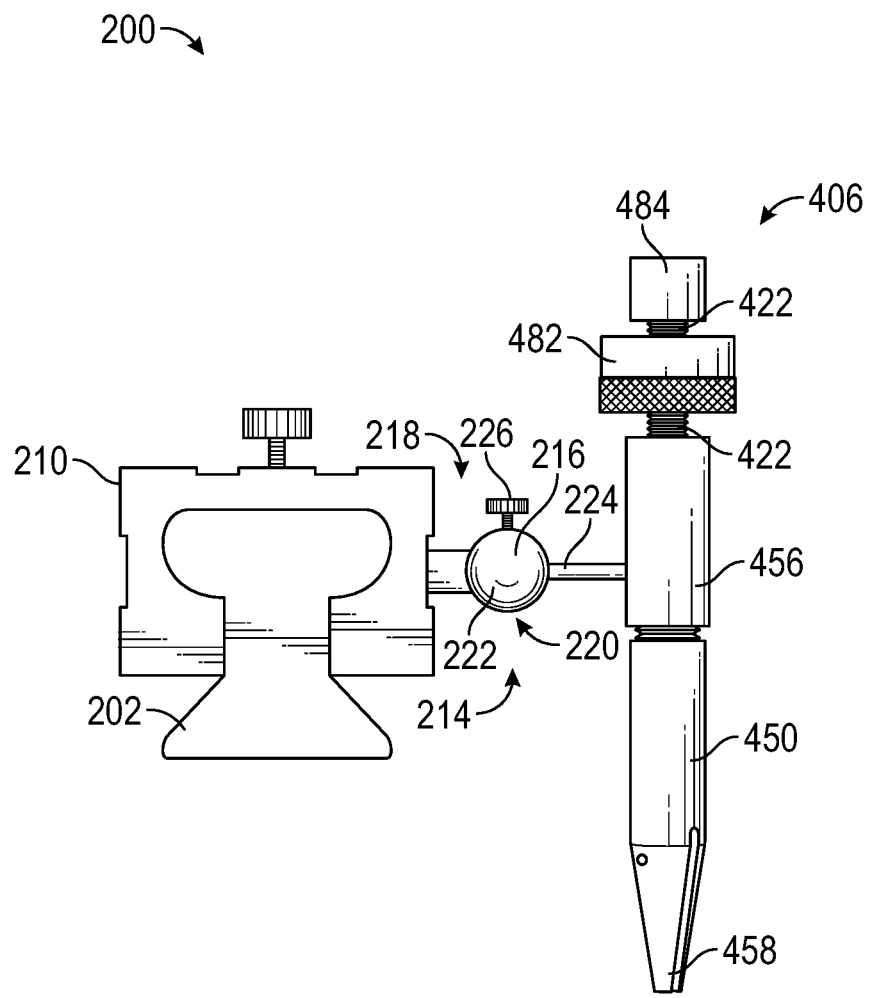
FIG. 15 is a side view of the third embodiment of a bone cutting device engaged to the apparatus of FIG. 2, according to aspects of the present disclosure.

FIG. 14 and FIG. 15 illustrate exemplary implementations of the osteotome 406. It is contemplated however that the osteotome 406 may accommodate other implementations where controlled surgical cuts are desired. In FIG. 14, the osteotome 406 may be grasped by a clinician or robotic device (not shown) or may otherwise be handheld to form a cut in bone tissue; e.g., parallel to a vertebrae 510 on a lamina 512.

Referring to FIG. 15, in some embodiments, the osteotome 406 may be implemented with the apparatus 200 described herein or otherwise be implemented in place of the osteotome 206. For example, the stem portion 224 of the apparatus 200 may be coupled to or mounted along the upper portion 430 of the osteotome 406. In this manner, the osteotome 406 may be oriented along different horizontal and vertical axes, and may be rotated relative to the fixed portion 202 of the apparatus 200 by nature of the osteotome 406 being coupled to the spherical joint 214. In this exemplary implementation, the osteotome 406 may be afforded any of the advantages and functionality of the osteotome 206 previously described; e.g., the osteotome 406 may be configured with multiple degrees of freedom, i.e., may be oriented along different horizontal and vertical axes relative to the fixed portion 202 of the apparatus 200 as previously described to provide precise, stable, and controlled cuts, and the like.

Exemplary Manufacturing Methods

In some embodiments, the osteotome 406 comprises components that are both machined and preconfigured. For example, components that may be machined include the body 410, the rod 422, the blade 424, the head 484, and the like, using a Mustang 60.

In some embodiments, the rod 422 may be formed using a stock piece of 0.50" diameter 1018 steel rod cut to a length of 7.50" using a chop saw. The cut end may then be faced on a lathe to a flat surface and to form a total length of 7.35". Using a mill, a centered 0.125" slot may then be cut 0.75" deep into the bottom portion of the rod 422. The rod 422 may then be rotated 90 degrees to machine the apertures 474 that accommodate the mating of the blade 424. The apertures 474 may have a 5/16" diameter counterbore formed using a plunge cut on the nearside of the slit 460 and a 0.136" diameter hole with a drill bit through both sides.

The head 484 may be machined using a 1.125" diameter piece of T-303 steel. Using a lathe, the top portion of the stock material being used may be faced. The diameter of the stock may then be faced down to a diameter of 1". A hole of 3/8" was may then be applied using a mill. A dye may then be used to create an internal thread (not shown) within the channel 485 to allow for the attachment onto the rod 422. The part may then be parted to the desired height and placed in the lathe to face to a flat surface. Chamfers may then be machined onto the top and bottom edges of the head 484.

The body 410 may be formed using a 1.125" diameter T-303 steel rod. In one embodiment, the upper portion 430 of the body 410 was faced down on the lathe to a desired diameter of 1.11". A 2.50" length portion of the rod 422 was then parted and faced where cut. Using a bit, the center of the body 410 was machined to its respective internal diameter. A 0.75" long portion on one end of the body 410 was left to face down the outer diameter to a smaller size to create external threads 444. The internal portion of the threads 446 was then machined down to an internal diameter of 0.516".

The lower portion 432 of the body 410 was faced down to its appropriate outer diameter and parted using the lathe. The end in contact with the bone was then shaped to its appropriate geometry using the right hand tool. A hole was then created on the opposite side of the piece 1.11" deep. The internal threads 446 were then machined in the body 410 using a tap in the mill. The slot 434 for the blade 424 was then formed using the mill.

The blade 424, and iterations thereof, were made using 303 stainless steel, 316L steel, and 440C stainless steel. A thin plate of stock from each material was faced on a mill to a thickness of 0.120". The four edges of each piece of material were then faced down to create flat surfaces. Using a mill cutter, based on the stock size of the material being used, four plunge cuts were made to create the insertion that will mate with the rod 422. The stock material was then flipped 180° to machine the blade 424 on the opposite end of the plunge cuts. Using the vertical band saw, each blade was then separated and faced on the mill to its desired geometry.

Testing and Analysis

Various tests were conducted to assess the efficacy of the embodiments described herein. For example, the following Weight Drop Test was conducted to assess the osteotome 406.

Weight Drop Test

Method: 10 lb weight dropped from a height of 17.2 cm above the osteotome 406 while the osteotome 406 was positioned by a surgeon for a standard Schwab grade 1 osteotomy. The weight was dropped repeatedly until the osteotome 406 entered the spinal canal or until 10 drops was reached, whichever came first. A single biomimetic spine model of an anatomically normal T12-L5 spinal segment with normal cortical and cancellous bone density was used for testing. The standard osteotome and the osteotome 406 were used on alternating sides of the spine model to account for any possible error with one side of the model having different bone quality than the other side. The first device used at each spinal level was also alternated to account for any possible error introduced by weakening of a spinal level after one side is tested.

RESULTS: The osteotome 406 achieved 10 weight drops at every tested level from T12-L5 without a single breach of the spinal canal or a neural foramen. The standard osteotome averaged 4.8 weight drops before entering the spinal canal (standard deviation 2.11). See Table 1 below for full results.

TABLE 1

Results of weight drop testing (Osteotome 406 = "Safe-T-Otome")

| Model Level | Device used/Number of Weight Drops | |
|---|---|---|
| | Left Side | Right Side |
| T12 | Osteotome/3 | Safe-T-Otome/10 |
| L1 | Safe-T-Otome/10 | Osteotome/5 |
| L2 | Osteotome/2 | Safe-T-Otome/10 |
| L3 | Safe-T-Otome/10 | Osteotome/7 |

TABLE 1-continued

Results of weight drop testing (Osteotome 406 = "Safe-T-Otome")

| | Device used/Number of Weight Drops | |
|---|---|---|
| Model Level | Left Side | Right Side |
| L4 | Osteotome/8 | Safe-T-Otome/10 |
| L5 | Safe-T-Otome/10 | Osteotome/4 |

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A device for forming an incision within bone tissue, comprising:
   a body defining a channel extending longitudinally at least partially from a proximal end of the body to a distal end of the body;
   a rod slidably engaged within the channel of the body;
   a blade coupled to a rod-blade interface of the rod along the distal end of the body and positioned at least partially within a slot defined along the distal end of the body;
   a head connected to a head portion of the rod proximate to the proximal end of the body for receiving a force to drive the rod through the channel and to move the blade at least partially through the slot; and
   a stopping mechanism engaged to the rod between the head and an upper portion of the body that is movable about the rod to preset a cutting depth of the blade relative to the body by limiting movement of the rod within the channel,
   wherein the stopping mechanism includes a quick quill stop including threads defined internally along the quick quill stop, the threads engaged to respective threads defined along a head portion of the rod, engagement of the threads of the quick quill top to the respective threads of the head portion of the rod maintaining the quick quill stop in a fixed position relative to the rod, and
   wherein the quick quill stop includes a button that releases the threads of the quick quill stop from the respective threads of the rod to accommodate free sliding movement of the quick quill stop along the rod.

2. The device of claim 1, wherein the quick quill stop includes a rotatable nut that accommodates incremental movement of the quick quill stop along the rod.

3. The device of claim 1, wherein the blade is at least partially positioned within a slit defined along the rod-blade interface.

4. The device of claim 1, wherein the body comprises stainless steel.

5. The device of claim 1, further comprising:
   a linear ball bearing oriented along the channel of the body, wherein a portion of the rod is engaged to the linear ball bearing to reduce friction and accommodate linear sliding engagement of the rod through the channel.

6. The device of claim 1, wherein at least a portion of the body is configured to be embedded within bone tissue.

7. The device of claim 1, further comprising:
   a barrel defined by the channel of the body and along a distal portion of the body;
   a handle defined along a proximal portion of the body opposite the distal portion;
   a spring engaged to the blade such that the blade is spring-loaded within the channel of the body;
   a ratchet defined along the body and engaged to the spring and blade to accommodate incremental movement of the blade through the channel; and
   a trigger defined along the body for releasing the spring to launch a cutting portion of the blade away from the proximal portion of the body.

8. A device, comprising:
   a body defining a channel extending longitudinally at least partially from a proximal end of the body to a distal end of the body;
   a rod slidably engaged within the channel of the body;
   a blade coupled to a rod-blade interface of the rod along the distal end of the body and positioned at least partially within a slot defined along the distal end of the body;
   a head connected to a head portion of the rod proximate to the proximal end of the body for receiving a force to drive the rod through the channel and to move the blade at least partially through the slot; and
   a stopping mechanism engaged to the rod between the head and an upper portion of the body that is movable about the rod to preset a cutting depth of the blade relative to the body by limiting movement of the rod within the channel,
   wherein the stopping mechanism includes a quick quill stop including threads defined internally along the quick quill stop, the threads engaged to respective threads defined along a head portion of the rod, engagement of the threads of the quick quill top to the respective threads of the head portion of the rod maintaining the quick quill stop in a fixed position relative to the rod, and
   wherein the quick quill stop includes a rotatable nut that accommodates incremental movement of the quick quill stop along the rod.

9. The device of claim 8, further comprising:
   a linear ball bearing oriented along the channel of the body, wherein a portion of the rod is engaged to the linear ball bearing to reduce friction and accommodate linear sliding engagement of the rod through the channel.

10. The device of claim 8, wherein the quick quill stop includes a button that releases the threads of the quick quill stop from the respective threads of the rod to accommodate free sliding movement of the quick quill stop along the rod.

11. A device, comprising:
   a body defining a channel extending longitudinally at least partially from a proximal end of the body to a distal end of the body;
   a rod slidably engaged within the channel of the body;
   a blade coupled to a rod-blade interface of the rod along the distal end of the body and positioned at least partially within a slot defined along the distal end of the body;
   a head connected to a head portion of the rod proximate to the proximal end of the body for receiving a force to drive the rod through the channel and to move the blade at least partially through the slot;
   a stopping mechanism engaged to the rod between the head and an upper portion of the body that is movable about the rod to preset a cutting depth of the blade relative to the body by limiting movement of the rod within the channel, wherein the stopping mechanism includes a quick quill stop including threads defined internally along the quick quill stop, the threads engaged to respective threads defined along a head portion of the rod, engagement of the threads of the quick quill top to the respective threads of the head portion of the rod maintaining the quick quill stop in a fixed position relative to the rod; and a linear ball bearing oriented along the channel of the body, wherein a portion of the rod is engaged to the linear ball bearing to reduce friction and accommodate linear sliding engagement of the rod through the channel.

12. The device of claim 11, wherein the quick quill stop includes a button that releases the threads of the quick quill stop from the respective threads of the rod to accommodate free sliding movement of the quick quill stop along the rod.

13. The device of claim 11, wherein the blade is at least partially positioned within a slit defined along the rod-blade interface.

* * * * *